United States Patent
Petrofsky (10) Patent No.: US 7,079,899 B2
(45) Date of Patent: Jul. 18, 2006

(54) WOUND HEALING WITH FEEDBACK CONTROL

(75) Inventor: Jerrold S. Petrofsky, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 372 days.

(21) Appl. No.: 10/605,132

(22) Filed: Sep. 10, 2003

(65) Prior Publication Data

US 2004/0147977 A1    Jul. 29, 2004

Related U.S. Application Data

(63) Continuation-in-part of application No. 10/506,911, filed on Sep. 2, 2004, and a continuation-in-part of application No. PCT/US03/07035, filed on Mar. 6, 2003.

(60) Provisional application No. 60/363,036, filed on Mar. 6, 2002.

(51) Int. Cl.
*A61N 1/08* (2006.01)
(52) U.S. Cl. ...................................................... 607/50
(58) Field of Classification Search .................. 607/50, 607/51, 63, 66–72
See application file for complete search history.

(56) References Cited

U.S. PATENT DOCUMENTS

| | | | |
|---|---|---|---|
| 3,760,812 A | 9/1973 | Timm et al. ................. | 128/418 |
| 4,738,250 A | 4/1988 | Fulkerson et al. ............ | 607/50 |
| 4,760,852 A | 8/1988 | Lekholm ..................... | 607/116 |
| 5,158,081 A | 10/1992 | McWhorter et al. .......... | 607/50 |
| 5,161,530 A | 11/1992 | Gamble ................... | 128/420 A |
| 5,423,874 A | 6/1995 | DAlerta ...................... | 454/251 |
| 5,433,735 A | 7/1995 | Zanakis ....................... | 607/50 |
| 5,861,016 A | 1/1999 | Swing ......................... | 607/50 |
| 5,974,342 A | 10/1999 | Petrofsky ..................... | 607/50 |
| 6,185,455 B1 | 2/2001 | Loeb ............................. | 607/3 |
| 6,334,069 B1 | 12/2001 | George ......................... | 607/2 |
| 6,353,763 B1 | 3/2002 | George ........................ | 607/50 |
| 6,393,326 B1 | 5/2002 | Nachum ...................... | 607/50 |
| 6,436,129 B1 * | 8/2002 | Sharkey et al. .............. | 607/96 |
| 6,512,955 B1 | 1/2003 | McEnany .................... | 607/72 |
| 6,562,037 B1 * | 5/2003 | Paton et al. .................. | 606/51 |

OTHER PUBLICATIONS

Akers TK, Gabrielson AL, "The effect of high voltage galvanic stimulation on the rate of healing of decubitus ulcers," Biomed. Sci. Instrum. 1984; 20:99-100.

(Continued)

*Primary Examiner*—Jeffrey R. Jastrzab
(74) *Attorney, Agent, or Firm*—David A. Farah; Sheldon & Mak PC (57) ABSTRACT

A method of promoting the healing of a wound disposed in soft tissue and having a physical extent is disclosed, comprising the steps of providing control circuitry to control the application of electrical current through a plurality of electrodes; applying three or more electrodes to the surface of the soft tissue around and in proximity to the wound, wherein each of the three or more electrodes is connected to the control circuitry; conducting an electrical current through the three or more electrodes, such that one electrode functions as a current source and one or more of the remaining electrodes functions as a current sink; and switching the function of acting as a current source and as a current sink among the electrodes. A device and suitable control circuitry are also disclosed. Feedback control is described.

11 Claims, 6 Drawing Sheets

OTHER PUBLICATIONS

Becker R, "The Body Electric," William Morrow, New York 1985.

Bradley M, Cullum N, Sheldon T, "The debridenment of chronic wounds: a systemic review," Health Technol. Assess. 1999; 3(17pt 1): 1-78.

De Astis V, Corbella A, Bafico F, Spinelli E, Porcu G, Bottari L, Petrini M, Maddeu V, "Decubitus lesions in patients referred to acute and post-acute home nursing care for the elderly in Genova," Assist. Inferm. Ric. 1999; 18:20-4.

Feedar J. Kloth L. Gentzkow G, "Chronic dermal ulcer healing enhanced with monophasic pulsed electrical stimulation," Phys. Ther. 1992; 72:539.

Franek A, Frenek E, Grzesik J, "Electrically enhanced damaged tissues healing. Part II: direct and pulse current in soft tissue healing." Pat Merkuriusz Lek, 1999; 40:198-201.

Kennedy EJ, "Spinal Cord Injury, the facts and figures," The University of Alabama Press, Birmingham, Alabama, 1999.

Knowles C, Horsy I, "Clinical evaluation of an electronic pressure-relieving mattress," Br. J. Nurs., 1999; 8:1392-5.

Lamid S, Ghatit EL, Smoking AZ, "Spasticity and pressure sores in spinal cord injured patients," Am. J. Phys. Med., 1983; 62:300-6.

Meehan M, "Beyond the pressure ulcer blame game: reflections for future," Ostomy Wound Manage, 2000; 46:46-52.

Petrofsky JS, "Functional electrical stimulation and the rehabilitation of the spinal cord injured patient," Adv. Clin. Rehab., 1987; 1:115-36.

Petrofsky JS, "Active physical therapy and its role in rehabilitation," Palestra, 8:23-28 1992a.

Petrofsky JS, "Functional electrical stimulation, a two-year perspective," J. Rehabilitation, 123:29-34 1992b.

Rowley BA, McKenna JM, Chase GR, Wolcott LE, "The influence of electrical current on an infecting microorganism in wounds," Ann. NY Acad. Sci., 1974b; 238:543-51.

Sapico FL, Ginunas VJ, Thornhill-Joynes M, Canawati HN, Capen DA, Klein NE, Khawam S, Montgomerie JZ, "Quantitative microbiology of pressure sores in different stages of healing," Diagn. Microbiol. Infect. Dis., May 1986; 5:31-8.

Senet P, Meaume S, "Decubitus sores in geriatric medicine. Local and general treatment of pressure sores in the aged," Presse Med., 1999; 28:1840-5.

Sugarman B, "Pressure sores and underlying bone infection," Arch. Intern. Med., 1987; 147:553-5.

Tavakoli K, Ruthowski S, Cope C, Hassal M, Barnett R, Richards M, Vandervord J, "Recurrence rates of ischial sores in para- and tetraplegics treated with hamstrings flaps: and 8-year study," Br. J. Plast. Surg., 1999; 52:476-9.

Witkowski JA, Parish LC, "Histophatology of the decubitus ulcer," J. Am. Acad. Deratol., 1982; 6:1014-21.

Mertz PM, Davis S, Arakawa Y, Cohen A, "Pulsed rg EGF treatment increased epithelialation of partial thickness wounds," J. Invest. Derm., 1988; 90:558.

Petrofsky JS, Kazemi A, Laymon MS, "The use of electrical stimulation of healing decubitus ulcers; a way to handle difficult wounds," Journal of Neurological and Orthopedic Medicine and Surgery, 2001: 20:114-117.

* cited by examiner

*Fig. 10* ns with Feedback Control

WOUND HEALING WITH FEEDBACK CONTROL

CROSS REFERENCE TO RELATED APPLICATIONS

This application is a continuation-in-part of International Application No. PCT/US03/07035, titled "Method and Device for Wound Healing" filed Mar. 6, 2003, and a continuation-in-part of U.S. patent application Ser. No. 10/506,911, titled "Method and Device for Wound Healing" filed Sep. 2, 2004, both of which claim, priority from Provisional Application No. 60/363,036, titled "System for Wound Healing" filed Mar. 6, 2002.

FEDERAL RESEARCH STATEMENT

This invention was made with United States Government support under Cooperative Agreement Number 0315 8879-01 with the National Medical Technology Testbed, Inc., United States Department of the Army. The United States Government has certain rights in this invention.

BACKGROUND OF INVENTION

Wounds heal quickly. Certain wounds are more susceptible than others to non healing. When bacteria can infiltrate a wound, such as in battle conditions or in older patients, the bacteria damage tissue and inhibit healing. In diabetic patients poor circulation and a large increase in tissue necrotic factor alpha and interleukin 2 prevent wounds from healing. Diabetic foot ulcers can result in amputation of limbs and many times are followed by death. About 70,000 amputations per year are linked to diabetic foot ulcers.

Pressure sores, also called decubitus ulcers, are injuries to the skin and underlying tissues caused by direct pressure over time to superficial tissues, including weight bearing over bony prominence, and shearing force on the skin. They can be exacerbated by excessive moisture on the skin, occlusion of lymphatic vessels, stress and smoking.

Pressure sores range from a very mild pink coloration of the skin, which disappears in a few hours, to a very deep wound extending through bone or into internal organs. These sores are classified in stages according to the severity of the wound. The most common scale to assess pressure sores is the National Pressure Ulcer Advisory Panel Scale which grades sores by 4 grades. Stage 1 is a non-blanchable erythema of intact skin. Stage II is partial loss of skin thickness where the ulcer presents as a skin abrasion. Stage III involves full loss of skin and necrosis to underlying fascia. Stage IV involves skin and fascia and or bone and muscle necrosis.

Pressure sores are a common medical problem causing substantial morbidity. For example, the incidence of pressure sores during hospitalization from stroke is 21%. The incidence of pressure sores is over 30% per year in patients with spinal cord injuries, and after hospitalization from stroke. The incidence of pressure sores is 41% in elderly patients discharged from a nursing home without stroke. In these cases, poor nutrition, moisture on the skin and heavy pressure on areas of the body from lying in bed causes the skin to break down. Even pregnant women in hospitals are susceptible to pressure sores.

Once pressure sores develop, they can take months to heal, or can remain chronically open sores. They often become infected leading to local abscess and septicemia, and have an average cost of medical care of $26,000 per wound.

Treatment of pressure sores include removal of the cause, the application of topical substances, debridement, and surgical procedures where the wounds are covered with tissue flaps. However, these treatments are often unsuccessful and, even when successful, are associated with a high recurrence rate.

Other types of soft tissue wounds may include, but not be limited to, diabetic ulcers, burns, and surgical incisions. Diabetic ulcers cause over 70,000 amputations a year in the United States alone. A method and system for treating such pressure sores and other soft tissue wounds would be desirable.

An estimated 16 million Americans are known to have diabetes, and millions more are considered to be at risk for developing the disease. Diabetic foot lesions are responsible for more hospitalizations than any other complication of diabetes. Among patients with diabetes, 15% develop a foot ulcer, and 12–24% of individuals with a foot ulcer require amputation. Indeed, diabetes is the leading cause of non-traumatic lower extremity amputations in the United States.

It is known to use electrical stimulation to promote healing of soft tissue wounds. Previous studies of electrical stimulation to treat pressure sores employed electrical stimulation with variation of stimulation parameters, such as current and waveform. Almost all modes of stimulation healed sores to some extent, but no studies optimized stimulation parameters. Additionally, the electrode placement and cross sectional area of the electrodes varied, the extent of the sores (stages I–IV) varied, as did the length of time the areas were stimulated.

The direction of the current (positive or negative) and the intensity of the current that optimizes wound healing varies in different phases of wound healing. A substantial body of research show that, while the direction or amplitude of current applied to a wound seems to always help healing, at certain phases of the process some currents work better. However, there has been little objective measure of the phases of wound healing in relationship to when to apply various currents and waveforms that enable optimizing healing for different types of wounds. It is generally known, for example, that in the initial few days after a wound injury, during the first inflammatory phase, skin generates a positive voltage potential. This positive potential, if enhanced, causes increased migration of white cells and increased clotting to the area in and around the wound. In contrast, after the first few days, to dissolve the clot and increase macrophage (white cell) or endothelial cells migration to the wound negative potentials are needed. But the amplitude of these potentials does not appear to be constant in different phases of wound healing. Further, little has been done to characterize the polarity and currents required for healing diabetic ulcers versus pressure sores, versus conventional wounds. Therefore, a great deal remains unknown in terms of when to apply a certain type of current and at what intensity to optimize healing.

Figure 1:
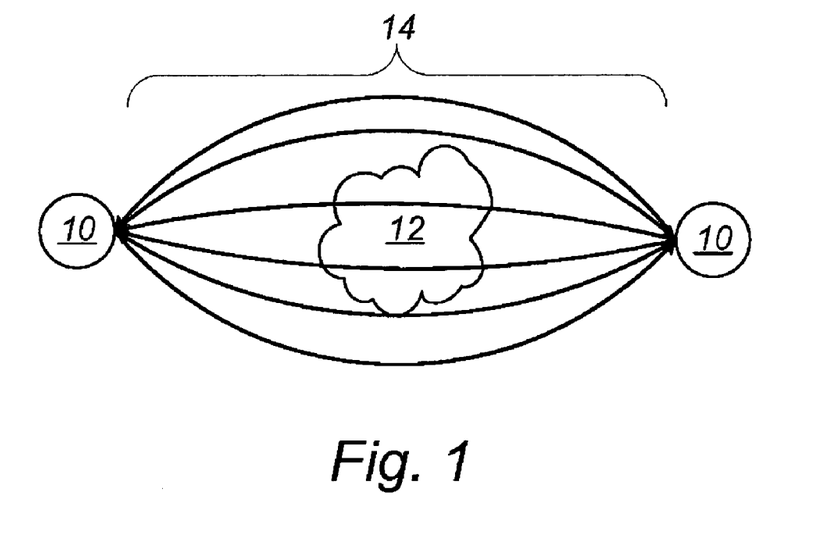
FIG. 1 is a block diagram of the lines of current flow across a wound between two electrodes, according to a prior art system.

For example, with reference to FIG. 1, one prior art system uses two electrodes 10 disposed closely adjacent to and on opposite sides of a wound 12 so that the path of current is across the wound. Modified square wave DC biphasic pulses are used, up to 100 pulses per second. Since the electrodes are placed across the wound, however, the electrical stimulation travels in a path of lowest resistance and the pattern of current flows between the two electrodes resemble that of Maxwell field lines as shown in FIG. 1, with the highest intensity through the center and intensity reduced exponentially, the further away the tissue is from the shortest line connecting the two electrodes. Therefore, for wounds that are irregularly shaped, or wounds that are deep such as stage 4 pressure sores, very little current actually travels into the wound, and electrical stimulation of such pressure sores results in low rates of healing. One reason diabetic ulcers don't seem to heal is that the epithelial layer builds on the edge of the wound, but growth factors are absent to cause migration to the center of the wound. With electrical stimulation, for whatever cause, the cells migrate.

What is known is that one of the most important processes in wound healing is re-epitheliazation. Studies using animals and man show that on the outside area of a wound, a strip of intact skin approximately 0.5 mm wide surrounds the wound. It is in this area that substantial voltage gradients occur. The mechanism by which cells migrate is poorly understood; however, the voltages generated by a typical wound, which can range as high as 120 mV/mm, are quite sufficient to cause cell migration and wound healing. For example, in one study on guinea pigs, it was shown that voltage gradients as low as 7 mV/mm caused substantial healing around wounds. A summary of the effect of currents on wounds is given below. Generally, negative currents (1) decrease edema around the electrode, (2) lyase or liquefy necrotic tissue, (3) stimulate growth of granulazation tissue, (4) increase blood flow, (5) cause fibroblasts to proliferate and make collagen, (6) induce epithelial cell margins to move, (7) attract neutrophils, and (8) stimulates neurite growth directionality. In contrast, positive currents (1) promote epithelial growth and organization, (2) act as vasoconstrictors and induce clumping, (3) denature protein, (4) aid in preventing post ischemic lipid peroxidation, (5) decrease mass cells in healing wounds, and (6) attract macrophages. Obviously different currents at different points in wound healing would be beneficial. However, up to this point no known device has been able to detect the optimal current to apply into each area of the wound. This is complicated further by the fact that wounds don't heal uniformly. One area of the wound may heal quite quickly while another area does not. This is common in pressure sores and diabetic ulcers. Generally, more superficial area of the wound heals very quickly whereas a deeper area of the wound may take months to heal but even in superficial wounds, one margin may heal more quickly than others due to drying or escar formation blocking healing. In this respect then, applying a positive current for a long period of time may be good for one part of the wound, but may be very poor for another portion of the wound, and may in fact inhibit healing. It is not surprising, then, that wounds seem to heal quickly with either positive current, negative current or alternating current. However, no one study has tried to divide the wound into healing sectors and optimize healing by varying the currents in different areas of a wound.

For these reasons among others, while therapists use electrical stimulation to treat pressure sores, there is no FDA approval of electrical stimulation for treatment of pressure sores or other soft tissue wounds. Further, conventional systems are expensive and complex. Therefore, it would be useful to have a system for the application of electrical stimulation to pressure sores that optimizes stimulation parameters. Further, it would be useful to have a system that a patient could use at home to apply electrical stimulation to a pressure sore. Still further, it would be useful to have a system that applied different currents at different points in wound healing, and which is able to detect the optimal current to apply into each area of the wound, and which divided the wound into healing sectors and optimized healing by varying the currents in different areas of a wound.

SUMMARY OF INVENTION

A method of promoting the healing of a wound disposed in soft tissue and having a physical extent is described comprising the steps of providing control circuitry to control the application of electrical current through a plurality of electrodes; applying three or more electrodes to the surface of the soft tissue around and in proximity to the wound, wherein each of the three or more electrodes is connected to the control circuitry; conducting an electrical current through the three or more electrodes, such that one electrode functions as a current source and one or more of the remaining electrodes functions as a current sink; and switching the function of acting as a current source and as a current sink among the electrodes. In one preferred embodiment, the step of switching proceeds in a sequence rotationally around the wound.

In another preferred embodiment, all remaining electrodes function as current sinks, and one or more of the remaining electrodes is connected to ground through an electrical resistance. Optionally, all electrodes functioning as current sinks are placed in series with electrical resistances set in the control circuitry, such that an electrical current flows into the physical extent of the wound. In a still further embodiment, the control circuitry is capable of measuring the electrical impedance between the electrode functioning as the current source and the one or more electrodes functioning as current sinks, and the measured electrical impedance is used to adjust the electrical resistances.

In another preferred embodiment, a distal electrode is applied to soft tissue remote from the proximate physical extent of the wound, wherein the distal electrode is connected to the control circuitry. Optionally, the remote soft tissue is on the opposite side of the body as the physical extent of the wound. Preferably, the distal electrode functions as a current sink. In another preferred embodiment, the switching is controlled to cause an electrical current to move helically into the physical extent of the wound.

In another embodiment, the healing of the wound from electrical impedance measurements is detected, and the pattern of stimulation is adjusted as the wound heals to optimize healing. In another embodiment, the control circuitry is capable of measuring an electrical impedance value between the electrode functioning as the current source and the one or more electrodes functioning as current sinks, the steps of applying, conducting, and switching are repeated in more than one treatment session, an electrical impedance value is measured in each treatment session, the measured impedance value is stored, and a healing rate for the wound is calculated from one or more stored impedance values.

Optionally, the electrical current can be an AC current. In one preferred embodiment, the electrical current alternates between a pulsital AC current, and a DC current.

In a still further embodiment, at least one of the electrodes is applied within the physical extent of the wound.

A method for promoting the healing of a wound disposed in soft tissue and having a physical extent is disclosed comprising the steps for providing three or more electrodes for application of electrical current to the soft tissue; conducting electrical current through the electrodes; causing one of the electrodes to function as a current source and one or more of the remaining electrodes to function as a current sink; and switching the function of acting as a current source and as a current sink among the electrodes.

A device for promoting the healing of a wound disposed in soft tissue and having a physical extent is described, comprising three or more electrodes; and control circuitry connected to the three or more electrodes to control the application of electrical current through the electrodes, the control circuitry capable of conducting an electrical current through the three or more electrodes such that one electrode can function as a current source and one or more of the remaining electrodes can function as a current sink and further capable of switching the function of acting as a current source and as a current sink among the electrodes.

In one preferred embodiment, the control circuitry is further capable of measuring the electrical impedance between the electrode functioning as the current source and the one or more electrodes functioning as current sinks.

In a further embodiment, one of the electrodes is adapted to be applied to soft tissue remote from the proximate physical extent of the wound.

In a still further embodiment, the control circuitry is capable of measuring an electrical impedance value between the electrode functioning as the current source and the one or more electrodes functioning as current sinks. Additionally, optionally the control circuitry is capable of conducting both a pulsital AC current, and a DC current.

A device for promoting the healing of a wound disposed in soft tissue and having a physical extent is described comprising three or more electrodes; means for conducting electrical current through the electrodes, connected to the three or more electrodes; means for causing one of the electrodes to function as a current source and one or more of the remaining electrodes to function as a current sink, connected to conducting means; and means for switching the function of acting as a current source and as a current sink among the electrodes, connected to the causing means.

A method of promoting the healing of a wound disposed in soft tissue and having a physical extent is described, comprising applying electrical stimulation as a function of electrical impedance measurement. In one embodiment, the electrical stimulation is an AC sine wave with about 250 microsecond pulse width and current of about −10 ma when the impedance is between about 3.7 to about 4.1 ohms per cm of tissue, and the electrical stimulation is an AC sine wave with about 250 microsecond pulse width and current of about −5 ma when the impedance is between about 4.8 and about 5.1 ohms per cm of tissue.

A method of promoting the healing of a wound disposed in soft tissue and having a physical extent and phase of healing is described, comprising determining the phase of healing and applying electrical stimulation as a function of the phase of healing. In a further embodiment, where the physical extent comprises a plurality of wound areas, the method further comprises determining the phase of healing in each of the plurality of wound areas, and applying electrical stimulation in each of the wound areas as a function of the phase of healing of that wound area. Preferably, in later phases of healing the electrical stimulation comprises a sine wave between about 220 to 250 microsecond pulse width.

A computer readable medium is disclosed containing program instructions sufficient to cause a user computer to operate control circuitry to determine the phase of healing of a wound disposed in soft tissue and apply electrical stimulation as a function of the phase of healing.

A system for promoting the healing of a wound disposed in soft tissue and having a physical extent and phase of healing is described, comprising a user computer system including computer readable memory, three or more electrodes, control circuitry connected to the three or more electrodes and the user computer to control the application of electrical current through the electrodes, the control circuitry capable of conducting an electrical current through the three or more electrodes such that one electrode can function as a current source and one or more of the remaining electrodes can function as a current sink, and measuring an electrical impedance value between the electrode functioning as the current source and the one or more electrodes functioning as current sinks; and a computer readable medium containing program instructions sufficient to cause the user computer to operate the control circuitry to determine the phase of healing of a wound disposed in soft tissue and apply electrical stimulation as a function of the phase of healing.

In a further embodiment where the physical extent comprises a plurality of wound areas, the program instructions are further sufficient to cause the user computer to operate the control circuitry to determine the phase of healing in each of the plurality of wound areas, and apply electrical stimulation in each of the wound areas as a function of the phase of healing of that wound area. Preferably, in later phases of healing the electrical stimulation comprises a sine wave between about 220 to 250 microsecond pulse width.

BRIEF DESCRIPTION OF DRAWINGS

These and other features, aspects, and advantages of the present invention will become better understood with reference to the following description, appended claims, and accompanying drawings, where:

DETAILED DESCRIPTION

The present invention is a method and device for applying electrical stimulation to soft tissue wounds, such as pressure sores, and is particularly useful with higher stage pressure sores and irregularly shaped pressure sores. The invention, however, can be used on a wide variation of soft tissue wounds, such as diabetic ulcers, burns, and surgical incisions.

Figure 2:
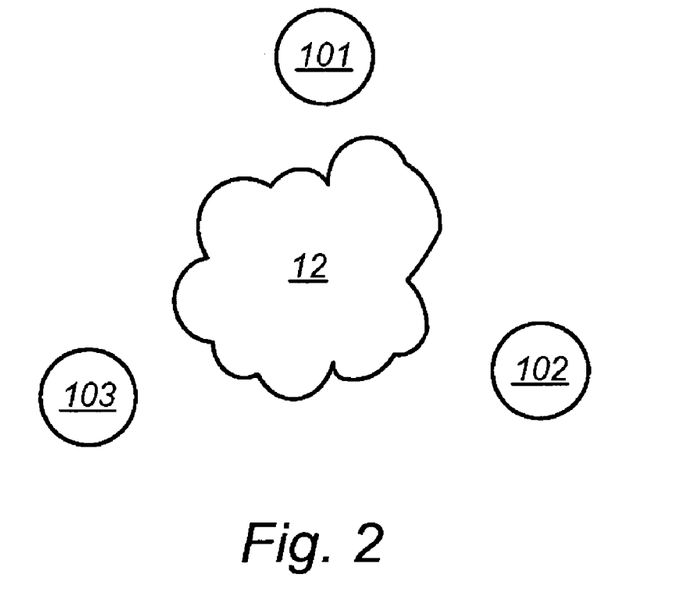
FIG. 2 is a block diagram of an electrode array placed around and in proximity to a wound, useable in one embodiment of the method of the invention.

With reference to FIG. 2, there is shown a diagram of placement of three electrodes 101, 102, 103 around and in proximity to soft tissue wound 12 according to one embodiment of the present invention. As can be seen, the three electrodes are labeled 101, 102 and 103. In use, when electrode 101 functions as a current source, electrode 102 and electrode 103 become reference electrodes and function as current sinks. In turn, when electrode 102 functions as a current source, electrode 101 and electrode 103 become reference electrodes and function as current sinks, and so on.

Although in this embodiment three electrodes are used, any plurality of three or more electrodes, such as four, five, or more electrodes could also be used. As will be known by those with skill in the art with reference to this disclosure, the electrodes can be constructed of any suitable electrically conductive material.

Figure 3:
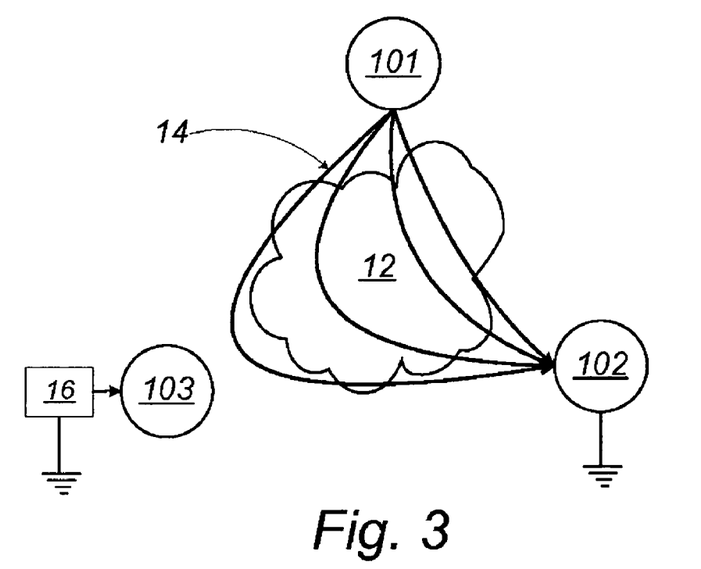
FIG. 3 is a block diagram of the electrical current flow in proximity to a wound, induced by one embodiment of the invention.

With reference to FIG. 3, in another embodiment, the system uses a switch, which may be analog, to vary the resistance to ground of two of the plurality of electrodes in sequence, such that an electrical current, represented by field lines 14, then flows from electrode 101 toward electrode 102 and slightly toward electrode 103. As shown in FIG. 3, when electrode 102 is given a solid ground, electrode 103 is given a soft ground through a resistor 16. The amount of this resistance is also variable and depends on the impedance of the wound, as will be understood by those with skill in the art with reference to this disclosure.

Figure 4:
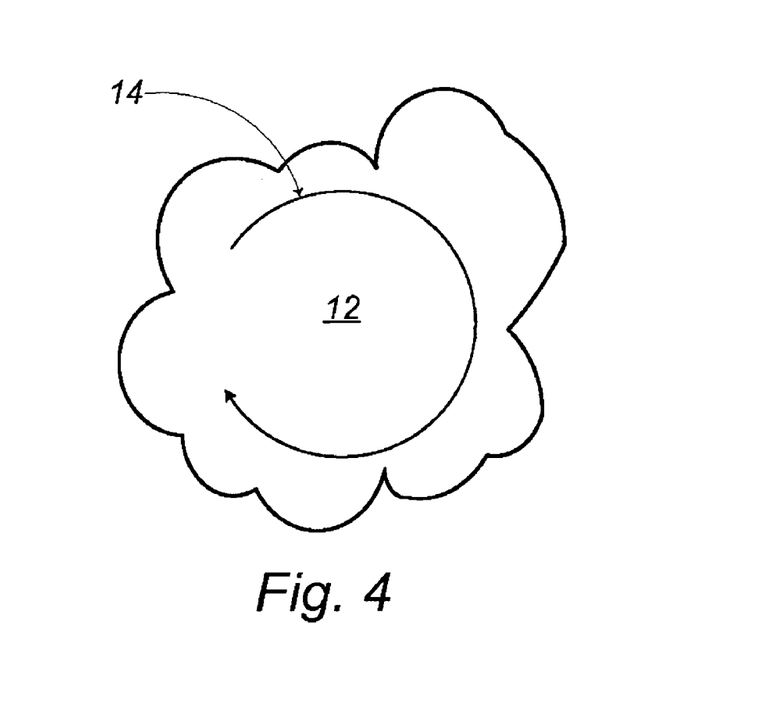
FIG. 4 is a block diagram of a rotational current pathway induced by another embodiment of the invention.

After a stimulus is applied through electrode 101, the stimulus is switched to go through electrode 102. Electrode 103 then becomes the hard ground electrode allowing a current path to flow between electrode 102 and electrode 103 with resistance 16 the applied between electrode 101 and ground, allowing some current flow across the wound and the rest to flow around the wound. After a stimulus is delivered through electrode 102, the process is repeated by switching the stimulus to go through electrode 103 so that an electrode 103 to electrode 101 pathway yields a high current pathway and a low current pathway is established between electrode 103 and electrode 102. By pulsing the stimuli in a circular motion around the wound, a current flow, represented by field lines 14, is established around the perimeter of wound, as well as across the physical extent of the wound, as shown in FIG. 4.

Figure 5:
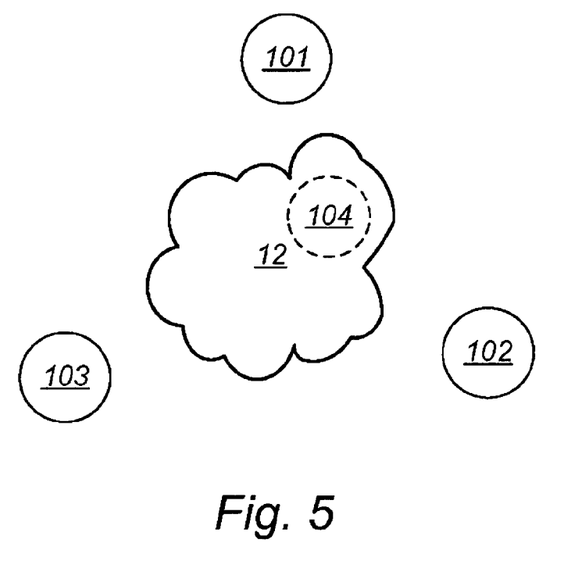
FIG. 5 is a block diagram of the electrode array of FIG. 2, with the addition of a distal electrode shown in outline, on a portion of the body opposing the location of the wound.

Referring now to FIG. 5, there is shown a diagram of a further method for electrical stimulation to a deep soft tissue wound, such as a stage 4 pressure sore, according to the present invention. As can be seen, in addition to electrode 101, electrode 102, and electrode 103 (or optionally more electrodes as determined by the embodiment in use) arrayed around and in proximity to wound 12, a distal electrode 104 (shown in outline) is applied on the opposite side of the soft tissue wound 12. For example, if the wound 12 is on a limb, distal electrode 104 would be on the opposite side of the limb from the wound.

Figure 6:
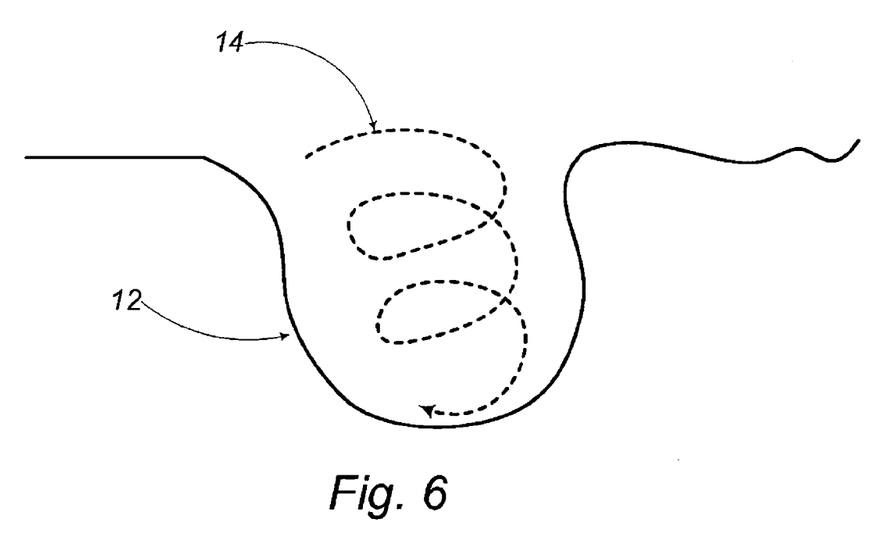
FIG. 6 is a cross-sectional block diagram of the wound of FIG. 5, showing the electrical current flow induced in a deep wound by that embodiment of the present invention.

When the electrode 101 applies stimulation, resistances are placed between electrode 102 and ground and electrode 103 and ground, creating a high current pathway between electrode 101 and distal electrode 104, and low current pathways between the remaining electrodes. This pattern is changed as electrical stimulation is rotated among electrode 101, electrode 102, and electrode 103 (or more electrodes). This allows a rotary electrical action around the surface of the wound, and also allows current to penetrate from three or more sides through the wound into the bottom of the wound. As shown in FIG. 6, this creates an electrical current 14 moving helically deep in the wound 12 (and toward a bone if disposed between the wound and distal electrode 104), in what may be called a whirlpool fashion, rather than merely across the surface of the wound.

Control Circuitry

Figure 7:
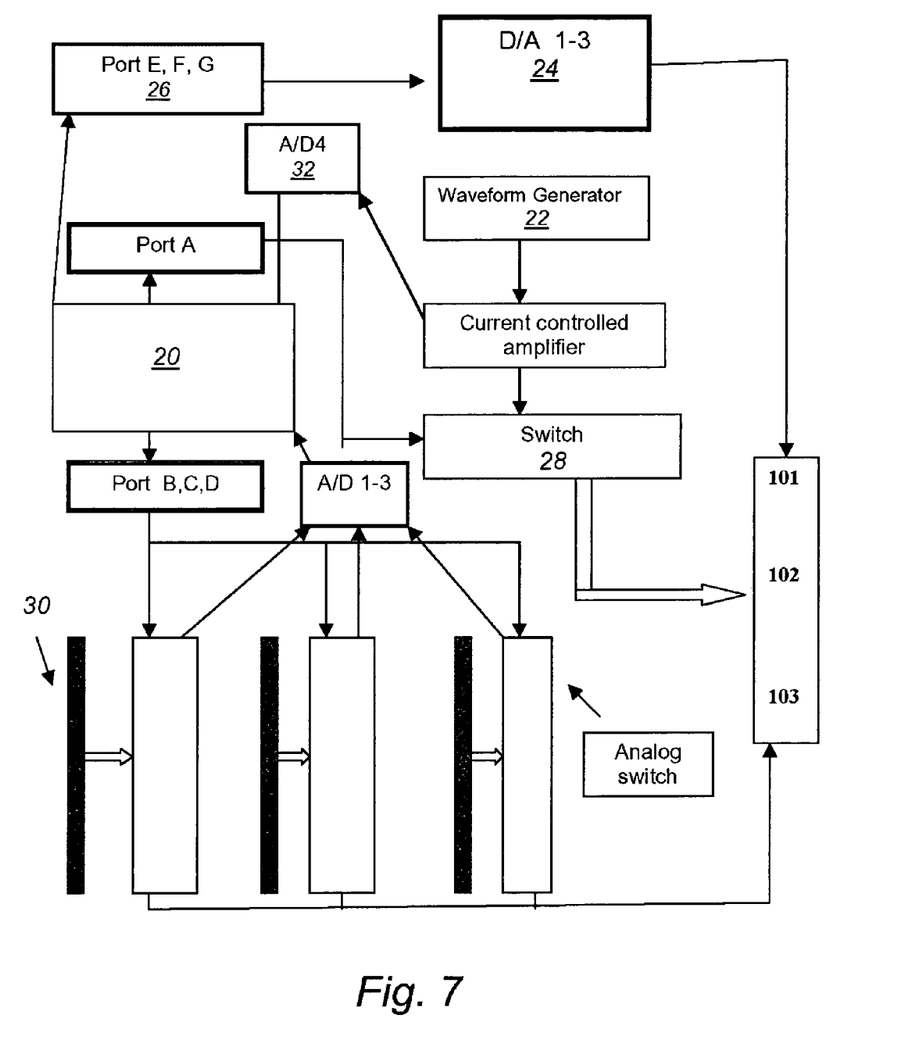
FIG. 7 is a block diagram of a circuit useable for control circuitry in one embodiment of the present invention.

Referring now to FIG. 7, there is shown a typical control circuitry useable in the present invention. Those skilled in the art with reference to this disclosure will be able to construct a suitable control circuit, and this circuit is disclosed as an example of what could be used to control the present invention.

As can be seen, a microprocessor 20 is used to control the electrode array. A sine generator 22 produces a sine wave output at 50,000 cycles per second. (Other waveforms could be used in an appropriate circuit.) The stimulator outputs are current controlled and are generated from a D/A converter (1-3) 24 from parallel ports E, F and G 26.

The electrode resistance is switched through an analog switch 28. A finite number of resistors 30 are used in a ladder such that a digital 8 bit word can select any of 256 different resistances.

The resister packs have 8 resistors; 0, 75, 100, 150, 200, 250, 500 and 1000 ohms. The common of the resister packs go to ground through a 10 ohm resistor. An output from this resistor is used to measure impedance on each electrode though an A/D converter. By comparing the input phase angle to the output phase angle through A/D4 32, the phase shift is calculated. The parallel ports can switch either electrode 101, electrode 102 or electrode 103 to ground directly through the analog switches or through single or combinations of resistors. For example, if a 1000 ohm and a 500 ohm resistor are both turned on, then the resistance of the electrode to ground is, according to Ohms law:

$$\frac{1}{R_t} = \frac{1}{R_1} + \frac{1}{R_2}$$

In this case, $R_t$ will equal 333 ohms.

In this manner, by turning on as many as all 8 channels of the switch, current is varied in the output loops.

The size of the resistor in the present system is typically 300 ohm and varies as a function of the tissue impedance. The size of the resistor is chosen as a multiple of tissue impedance to bend the current. For example, if it is assumed that the tissue impedance is 800 ohms, a 300-ohm resistor is used to bend one third of the current across the wound and the majority of the current is in line between the perimeter electrodes. However, this can be adjusted to vary the amount of current going into the wound by varying the resistor tied in series with the electrodes during rotary stimulation.

Tissue impedance is measured dynamically in between impulses. As an electrode finishes firing, the pathway between that electrode and next electrode is used to measure tissue impedance. A 100 microamp subliminal current is applied in between each stimulus between any two electrodes to measure the impedance of the tissue across the wound. The frequency in the exemplar embodiment is 50,000 cycles per second. (As will be known to those skilled in the art with reference to this disclosure, although a sine wave is used in this embodiment, other waveforms and frequencies can be generated.) This current, then, travels through the wound and provides a measure of the impedance of the wounds such that as the wound heals or if the wound gets dry or wet during the stimulation process, the impedance of the electrodes changes dynamically to always provide the same extent of bending of the current around the wound. In this manner, a whirlpool electrical current flows around and into the wound to heal the superficial wound when stimulated with an appropriate waveform.

In different studies, different investigators have stated that pulsital AC currents and DC continuous low-level micro amp currents work best to heal wounds. The electrical current during stimulation in the present system is a combination of AC, and DC currents. To take advantage of both types of current, the electrical current delivered by the electrodes of the present system preferably comprise pulsital AC current as the function of current source is rotated between the electrodes 101, electrode 102, and electrode 103, and in the interval between the application of pulses between the electrodes, a 100 microamp DC current is applied. Therefore, in one preferred embodiment, both AC and DC current are applied through the electrodes to maximize wound healing.

Figure 8:
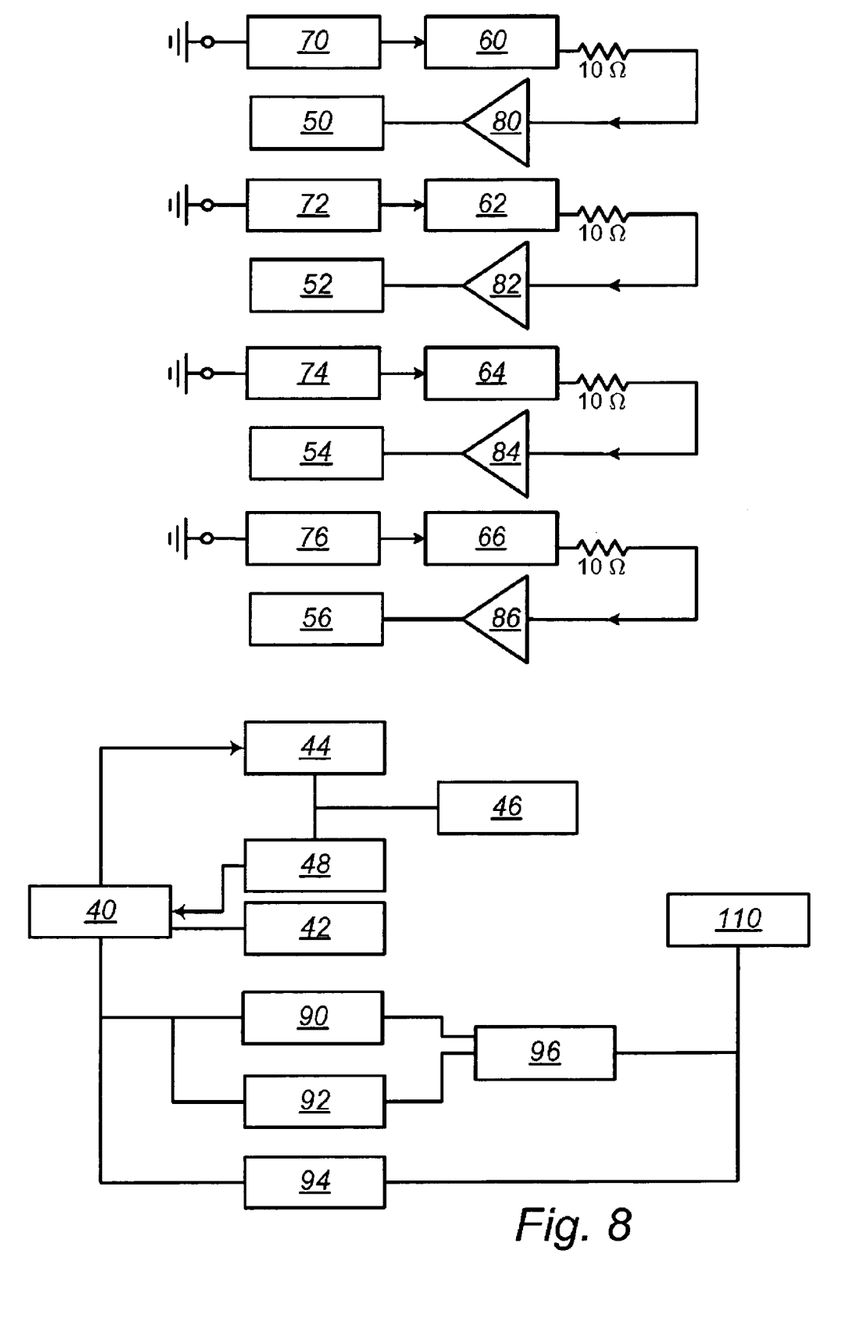
FIG. 8 is a block diagram of another circuit useable for control circuitry in another embodiment of the present invention.

Referring now to FIG. 8, there is shown a diagram of another embodiment of a control circuit for four electrodes. Microprocessor 40 communicates with parts of the stimulator through digital to analog (D/A) and A-D converters and through a gate array chip 42.

The microprocessor 40 has several functions. First, the microprocessor controls a sine wave generator 44 and selects a frequency of the generator at either 10, 25 or 50 kilocycles. The output of the sine wave generator 44 is kept constant with the constant current amplifier at a current of one milliamp.

In one embodiment, the microprocessor 40 does not generate the sine wave because the frequency of the sine wave is too high for the microprocessor to maintain output and to provide high enough rates of data input and output to control the sine wave generator directly. Therefore, the sine wave generator 44 is preferably a discreet chip. The output of the chip is switched between electrodes 101, 102, 103 and 106 by an analog switch 46. The analog switch 46 is controlled through the gate array 42 that is also controlled through the microprocessor 40.

The sine wave output is applied through the electrodes and the amplitude and phase of the sine wave are detected through an analog digital converter. The analog digital converter is shown on the diagram as A/D-4 48. The analog digital converter is a 12-bit analog to digital converter and provides an input to the microprocessor 40, showing the phase and amplitude of the sign wave being generated into the analog switch. Once the sine wave output is applied to the skin, it is sampled through A-D converters AD-0 50, AD-1 52, AD-2 54, and AD-3 56.

A 10 ohm resistor is in series with analog switches 60, 62, 64 and 66. The analog switches are switched by the microprocessor through the gate array 42 such that each electrode 101, 102, 103 and 106 can either be switched to a ten-ohm resistor as shown on the diagram directly to ground or through a series of resistors to ground.

The resistor packs 70, 72, 74, and 76 are headers that hold 12 resistors. One resistor is a straight wire going to ground while another is a 22 mega-ohm resistor. The rest of the resistors are set such that a variable resistance can be selected from the analog switches (60, 62, 64, and 66) for each electrode so that a variable resistance can be set from each of the respective electrodes to ground. The analog switches shown in 60, 62, 64, and 66 are all controlled by gate array 42 such that 12 individual analog switches can be selected. By allowing individual switch selection, combinations of resistors can be used so that rather than 12 discreet impedances between electrodes 101, 102, 103, 106 and ground, by selecting combinations of switches, to be either off or on in the analog switches 60, 62, 64, and 66, the number of potential resistances to ground become selectable as 2 to the 212 possible impedances.

Each resistor in resistor packs 70, 72, 74, and 76 are one-tenth watt resistors. An operational amplifier is connected from each 10 ohm resistor as shown in the diagram as operational amplifiers 80, 82, 84, and 86 such that the output across the 10 ohm resistors is amplified with a gain of 100. The amplified output is then fed back to the microprocessor through A-D converters 50, 52, 54 and 56. In this way, then, if the resistor packs are set such that the 10 ohm resistor is shorted to ground, the amplitude and phase angle of an impedance generated by chips 44 and 46 can be measured at the 10 ohm resister. By measuring the amplitude and phase angle, a complex impedance change across the outputs of electrodes of 101, 102, 103 and 106 can therefore be calculated. Analog digital converters 50, 52, 54 and 56 are also 12-bit analog to digital converter chips with a speed of at least 20,000 samples per second.

Therefore, the impedance across any pair of electrodes can be measured by selecting an output in analog switch chip 46 to provide an output to either electrode 101, 102, 103 or 106 and then by selecting the appropriate input through analog switches 60, 62, 64 and 66 from electrode 101, 102, 103 or 106, the appropriate electrode pair can be sampled and impedance can be measured through A-D converters 50, 52, 54, and 56. Phase angle can be measured by cross comparing the phase of the sine wave between A-D 4 48 and A-D 0 50, A-D 1 52, A-D 2 54 and A-D 3 56.

The stimulator output can also be switched between electrodes 101, 102, 103 and 106 when impedance is not being measured. Since the stimulator output will also be selected on leads to the electrodes, analog switch chip 46 must be switched off during electrical stimulation. Therefore, chip 46 has an output that can be either switched to leads to the electrodes or set to infinity. This can be accomplished by tri-stating chip 46 or having a fifth output where the output is switched to an output that is not switched to the body. In between, stimulation impedance can be measured. During stimulation, chip 46 is turned off. During actual stimulation itself, the stimulation is a sine wave, or other desired wave, that is generated from D/A converters 90 and 92. D/A 90 generates the actual sign wave stimulus output 96 whereas D/A 92 controls the amplitude. The sine wave is set at a frequency of 10 to 50 cycle impulses per second and pulse width between 1000 and 1000 microseconds by the computer. The amplitude is variable and is controlled by D/A 92 between 0 and 25 milliamps. In addition, a DC offset can be provided in between stimulation with the sine wave through D/A 94. D/A 94 is also a 12-bit D-A converter as is D-A 90 and D/A 92 and provides a 0 to 5 milliamp DC offset. This offset can be switched either mixed with the sine wave or can be provided independently to leads to the electrodes in between sine wave generation. Therefore, the two independent outputs go to analog switch 110 and analog switch 110 can switch either one lead into output 1, 2, 3 and 4 or both waves together into 1, 2, 3, or 4. Analog switch 110 is also controlled by the gate array 42. Sin summary, chip 46 switches the sine wave to measure impedance while chip 110 switches the electrical stimulation output which can be either AC, DC or both mixed together.

Feedback Control of Wound Healing

The whirlpool electrode will allow currents to be positive in one area of a wound or negative in another. However, in a further embodiment, currents may be adjusted as a function of wound healing. With feedback from the wound as to the degree of healing, information can be provided to a computer, which can then make a decision as to which currents to apply to the wound at what time, and in which areas of the wound to optimize healing in different segments of the wound. The operation can also be done manually, or in conjunction with a computer. In other words, if it is determined that one portion of the wound is healing very slowly, and there is excessive bleeding, a positive current may be applied, whereas in the other areas of the same wound the operator (including automatic operation by a computer) may switch to a negative current to optimize healing in these areas.

It must be determined which areas of the wound are healing and which are not. This can be accomplished by using tissue voltages and/or tissue impedance. Tissues generate a voltage as mentioned above, when there is a wound. That voltage, which goes very positive at the early stages of the wound, exponentially decays back to only a few millivolts after the wound is healed. Therefore, the fresher the wound is, or the more unhealed the wound is, the higher the electrical voltage being generated in that area of the wound.

Tissue impedance is complimentary to current generation. If current is being generated by a portion of the wound, then impedance would be high, since impedance is the resistance to the movement of an electric current. If the tissue generates a current, then the current developed by two electrodes will be opposed by the current generation in the wound. In other words, impedance across a wound will vary as a function of the healing process. These measures of impedance around the wound then would provide information as to the degree of healing of the wound. After impedance is measured across any two electrodes, stimulation current (either positive, negative or alternating) as taught above, will be applied through that electrode pair at the appropriate amplitude to optimize wound healing.

With, for example, three pairs of electrodes, three completely separate patterns of stimulation can be used around the wound as the electrodes switch from the first to the second to the third electrode and then back to the first again. Thus, with either three, four or more electrodes, areas of the wounds that are not healing are treated very different from areas that do heal, and feedback through impedance provides an optimization of wound healing.

If the wound heals evenly across the entire wound, then impedance will change continuously as well as during wound healing. However, what usually happens is that one portion of the wound heals faster than the other. Consider, for example, an elliptical wound with three electrodes surrounding it: A, B and C. Impedance is measured between point A and B, followed by a pulse of electrical stimulation. Impedance is then measured from point B to C followed by a pulse of electrical stimulation. Impedance is then measured from point C to A followed by a pulse of electrical stimulation. If impedance between A and B shows the wound is not healing, then the stimulation amplitude and pulse waveform will be different than if the impedance is lower from B to C, and C to A, and so on. In other words, there are three different pulses applied to the wound covering three different portions of the wound. The stimulation waveform and intensity can be varied for each third of the wound as a function of healing.

A method to use feedback control is now described. A stimulation sequence is started on a first electrode (step 200). Impedance is then measured between the active electrode and other electrodes, and a phase of healing is then determined from the impedance measurement (step 202). The appropriate stimulation current and polarity between the active electrode and other electrodes is then calculated, based upon the phase of healing (step 204). Stimulation incorporating the feedback is then done (step 206). The process begins again at step 200.

With more than the three electrodes shown described above, more of the wound could be controlled, or the current fields can be bent by varying the resistance to ground on electrodes A and C when B becomes active, as an example, so that the shape can also be changed of the stimulation field as well as the current pattern.

The shape of the electrical field when stimulated through A, B or C can be changed as taught above, so that the whole wound is covered, and as the wound heals the current waveform and amplitude between each pair of electrodes can be changed as a function of the healing across that area of the wound.

Figure 9:
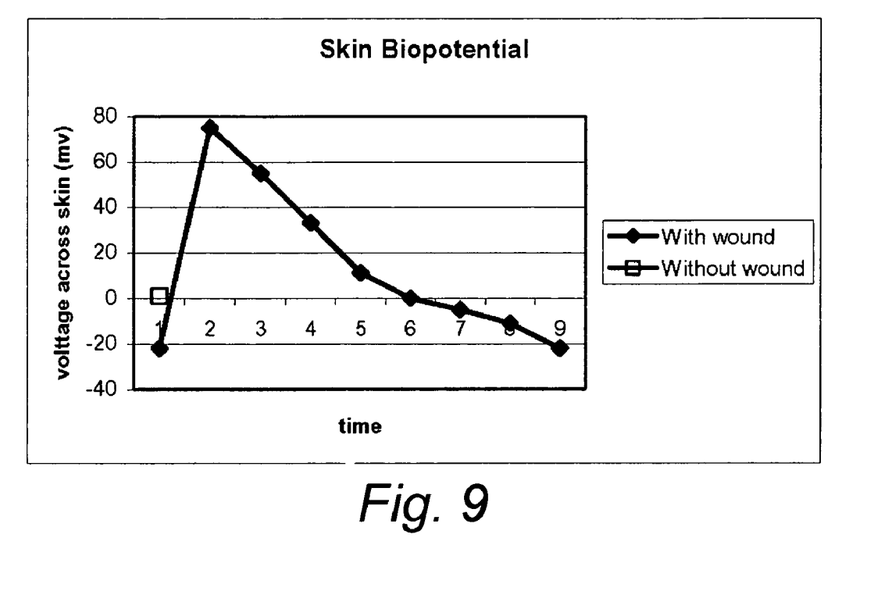
FIG. 9 is a graph showing skin biopotential across a wound as a function of healing time.

The skin biopotentials from good skin on the leg are about −20 mv. When a wound occurs, the skin reverses potential and goes to about +80 mv. As the wound heals, the voltage is reduced back to negative again. With reference to FIG. 9, a skin biopotential as a function of time resulting from a typical wound on good skin is shown. The time units are arbitrary, as healing may take 1 week, or 2 years, and therefore there is no linear timescale.

In the initial skin destruction and inflammatory phase of wound healing the voltage across the skin ranges from about 77 mv to about 55 mv. Here the wound is open and dead tissue is removed by white cells. In the reparative phase, epithelial cells migrate across wound and collagen is laid down, and potentials range from about 55 mv to about −10 mv. In the remodeling phase, the skin strengthens and heals and remodels, and voltages range from about −10 mv to about −20 mv.

Using trendline analysis it is possible to create trendlines to fit the observed data. For example, using the data of FIG. 11 a possible polynomial trendline would be shown in Equation 2:

$$v = -0.18t^4 + 3.04t^3 - 15.8t^2 + 9.14t + 78.8$$

Correlations between phase of wound healing and impedance will vary with the presence of such conditions as diabetes. One measurement of impedance in typical skin, in ohms per cm of tissue, measured between two electrodes at a frequency of 50,000 cycles per second, is shown in Table 1.

TABLE 1

| Phase | Description | Impedence |
|---|---|---|
| Phase 1 | Start | 5.2 |
| Phase 1 | Early inflamatory | 7 |
| Phase 1 | Late inflamatory | 3.1 |
| Phase 2 | Early reparative | 3.7 |
| Phase 2 | Late reparative | 4.8 |
| Phase 3 | Remodeling | 5.1 |

Table 2 correlates different phases of wound healing and the amplitudes of current used for typical wound healing in normal wounds in non-diabetic subjects. This is a typical example of how the method would work, correlating determining the phase of healing (as per Table 1) and applying electrical stimulation as a function of the phase of healing (Table 2). The AC current is a sine wave.

TABLE 2

| Phase | Description | Stimulation |
| --- | --- | --- |
| Phase 1 | Start | DC +1 ma |
| Phase 1 | Early inflammatory | DC −5 ma |
| Phase 1 | Late inflammatory | AC −10 ma |
| Phase 2 | Early reparative | AC −10 ma |
| Phase 2 | Late reparative | AC −5 ma |
| Phase 3 | Remodeling | AC −5 ma |

It is known in the art to apply positive DC current in the first few days after a wound starts, to help attract white cells to the area and aid in clotting, and after that, change the DC current to negative. Instead of using a negative DC current throughout wound healing, however, AC current (a sine wave at about 250 microsecond pulse width) seems to work best. A sine wave between about 220 to about 250 microsecond pulse width will also work. A range of 100 microseconds to 1000 microseconds and mono and biphasic can be used. Burns, etc., may require different stimulation patterns.

Figure 10:
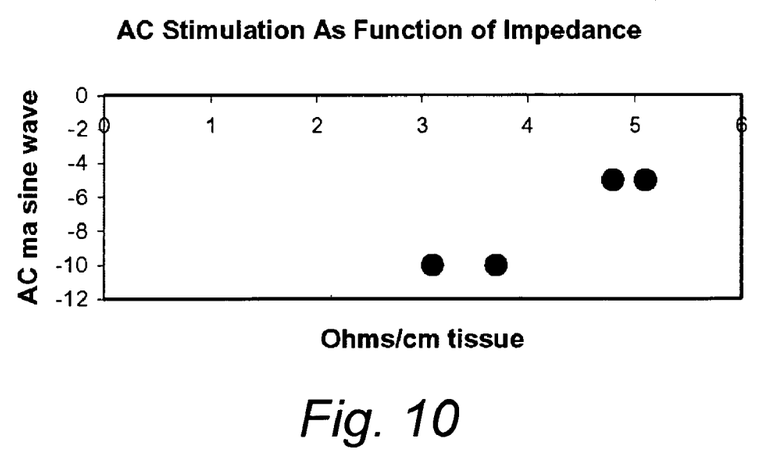
FIG. 10 is a graph showing a correlation between impedance and electrical stimulation for phases of wound healing beyond early inflammatory, according to one embodiment of the invention.

As can be seen in the tables, after the initial early inflammatory stage of Phase1, when the impedance is between about 3.1 to about 3.7 ohms per cm of tissue, the electrical stimulation is an AC sine wave with about 250 microsecond pulse width and current of about −10 ma. When the impedance is between about 4.8 and about 5.1 ohms per cm of tissue, the electrical stimulation is an AC sine wave with about 250 microsecond pulse width and current of about −5 ma. Those skilled in the art will understand the use of the qualifier "about" as reference to the normal degree of uncertainty inherent in measurement. These values are shown in FIG. 10, for phases later than early inflammatory.

It must be emphasized, however, that these currents may vary with diabetic wounds, versus burns, versus normal wounds. It is very possible, that with the reduction in the nerve supply to the skin in people with diabetes, that the voltages will vary a great deal and so will the impedance during wound healing. This also may be true of patients on strong immuno-suppressant drugs. Some degree of empirical testing will be needed to determine the particular correlation that works best for the subject being treated.

This feedback calculations can be implemented in a simple spreadsheet format that can be done by hand, or by using computerized spreadsheet programs such as Microsoft Excel(r), or other available programs as will be known to those skilled in the art. Further automated operation of the feedback control are also possible. It will be understood by those skilled in the art that variations in the described embodiment are possible, and that specific aspects of this embodiment are not limitations on the claimed invention. When using automated feedback under control of a management program, it will be preferable to store the program on a hard drive memory of a computer which is connected to the control circuitry. An optional printer permits printing of reports. An appropriate user interface on the computer is preferred for operator interaction with the management program. A series of prompts can appear on the user interface on computer, guiding an operator to appropriate stimulation, and implementation of the feedback control.

As will be known in the art with reference to this disclosure, it would be possible to store a management program having instructions sufficient to implement the feedback control of the present invention on any computer readable medium, such as floppy drives, dismountable hard drives, DVDs, CD-ROM, CD-R, CD-RW, memory cards, and the like. It would be possible to implement the management program on any type of personal computer, such as a Pentium(r) class machine. Operating systems useable include those available from Microsoft(r), including Windows(r) 98, ME, 2000, and XP. The computer memory can be any media useable for storage of computer data, including but not limited to hard drives, floppy drives, removable drives, RAM, ROM, DVDs, and CD-R.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Also, any element in a claim that does not explicitly state "means for" performing a specified function or "step for" performing a specified function, should not be interpreted as a "means" or "step" clause as specified in 35 U.S.C. §112.

Although the present invention has been discussed in considerable detail with reference to certain preferred embodiments, other embodiments are possible. For example, so long as there is at least one electrode functioning as a current source and one functioning as a current sink, it would be possible to have only some of the electrodes act as current sinks. Further, the application of a distal electrode according to the invention would be possible at various sites remote from the proximate physical extent of the wound. In an even further embodiment, the distal electrode could be switched to function as a current source, with one or more electrodes around and in proximity to the wound acting as current sinks. In a still further embodiment, impedance values between the current source electrode and current sink electrodes could be measured in multiple treatment sessions, stored, and used to calculate a healing rate for the wound as the impedance values changed. Impedance measurements might be done at different frequencies, for example 1,000 cycles per second. Therefore, the scope of the appended claims should not be limited to the description of preferred embodiments contained in this disclosure.

The invention claimed is:

1. A method of promoting the healing of a wound disposed in soft tissue and having a physical extent, comprising applying electrical stimulation utilizing three or more electrodes, said three or more electrodes each configured to act intermittently as a current source or a current sink, as a function of electrical impedance measurement.

2. The method of claim 1, where the electrical stimulation is an AC sine wave with about 250 microsecond pulse width and current of about −10 ma when the impedance is between about 3.7 to about 4.1 ohms per cm of tissue, and the electrical stimulation is an AC sine wave with about 250 microsecond pulse width and current of about −5 ma when the impedance is between about 4.8 and about 5.1 ohms per cm of tissue.

3. A method of promoting the healing of a wound disposed in soft tissue and having a physical extent and phase of healing, comprising determining the phase of healing and applying electrical stimulation utilizing three or more electrodes, said three or more electrodes each configured to act intermittently as a current source or a current sink, as a function of the phase of healing.

4. The method of claim 3, the physical extent comprising a plurality of wound areas, further comprising determining the phase of healing in each of the plurality of wound areas, and applying electrical stimulation in each of the wound areas as a function of the phase of healing of that wound area.

5. The method of claim 3, where the electrical stimulation comprises a sine wave having between about 220 microsecond and about 250 microsecond pulse width.

6. The method of claim 3, where the electrical stimulation comprises a sine wave having between 100 microsecond and 1000 microsecond pulse width.

7. A computer readable medium containing program instructions sufficient to cause a user computer to operate control circuitry to determine the phase of healing of a wound disposed in soft tissue and apply electrical stimulation utilizing three or more electrodes, said three or more electrodes each configured to act intermittently as a current source or a current sink, as a function of the phase of healing.

8. A system for promoting the healing of a wound disposed in soft tissue and having a physical extent and phase of healing, comprising:
   a user computer system including computer readable memory, three or more electrodes;
   control circuitry connected to the three or more electrodes and the user computer to control the application of electrical current through the electrodes, the control circuitry capable of conducting an electrical current through the three or more electrodes such that one electrode can function as a current source and one or more of the remaining electrodes can function as a current sink, and
   measuring an electrical impedance value between the electrode functioning as the current source and the one or more electrodes functioning as current sinks; and
   a computer readable medium containing program instructions sufficient to cause the user computer to operate the control circuitry to determine the phase of healing of a wound disposed in soft tissue and apply electrical stimulation as a function of the phase of healing.

9. The system of claim 8, the physical extent comprising a plurality of wound areas, the program instructions further sufficient to cause the user computer to operate the control circuitry to determine the phase of healing in each of the plurality of wound areas, and apply electrical stimulation in each of the wound areas as a function of the phase of healing of that wound area.

10. The system of claim 8, where the electrical stimulation comprises a sine wave having between about 220 microsecond and about 250 microsecond pulse width.

11. The system of claim 8, where the electrical stimulation comprises a sine wave having between 100 microsecond and 1000 microsecond pulse width.

* * * * *